(12) United States Patent
Kim et al.

(10) Patent No.: US 10,378,054 B2
(45) Date of Patent: Aug. 13, 2019

(54) SOL-GEL CHIP USING POROUS SUBSTRATE FOR ENTRAPPING SMALL MOLECULES AND SCREENING METHOD OF SMALL MOLECULES SPECIFIC MATERIAL USING THEREOF

(71) Applicant: Dongguk University Industry-Academic Cooperation Foundation, Seoul (KR)

(72) Inventors: So Youn Kim, Seoul (KR); Ji Young Ahn, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 30 days.

(21) Appl. No.: 13/751,074

(22) Filed: Jan. 26, 2013

(65) Prior Publication Data
US 2013/0210637 A1 Aug. 15, 2013

(30) Foreign Application Priority Data
Feb. 13, 2012 (KR) .................. 10-2012-0014378

(51) Int. Cl.
C12Q 1/68 (2018.01)
C12Q 1/6876 (2018.01)
G01N 33/543 (2006.01)

(52) U.S. Cl.
CPC ....... *C12Q 1/6876* (2013.01); *G01N 33/5436* (2013.01); *G01N 33/54386* (2013.01); *B01J 2219/0072* (2013.01); *B01J 2219/0074* (2013.01); *B01J 2219/00641* (2013.01); *B01J 2219/00725* (2013.01)

(58) Field of Classification Search
None
See application file for complete search history.

(56) References Cited

U.S. PATENT DOCUMENTS

| | | | | |
|---|---|---|---|---|
| 2006/0121474 | A1* | 6/2006 | Kim et al. ................ | 435/6 |
| 2007/0015175 | A1* | 1/2007 | Kumar ............ | G01N 33/56983 |
| | | | | 435/6.11 |
| 2007/0275480 | A1* | 11/2007 | Brander et al. ............. | 436/501 |
| 2008/0090074 | A1* | 4/2008 | Matsumura et al. ......... | 428/338 |
| 2008/0254082 | A1* | 10/2008 | Toledano ............. | A01N 25/28 |
| | | | | 424/408 |

FOREIGN PATENT DOCUMENTS

| | | |
|---|---|---|
| KR | 10-0784437 B1 | 12/2007 |
| KR | 10-0794186 B1 | 1/2008 |
| KR | 10-2011-0081808 A | 7/2011 |

OTHER PUBLICATIONS

Ahn et al. Analytical chemistry 84.6 (2012): 2647-2653 and Supplementary Materials.*
Ahn et al. Molecular and Cellular Toxicology, Jun. 30, 2008, pp. 100-105, vol. 4, No. 2.*
Steinhauer et al. Anal. Biochem. 341 (2005) 204-213.*
Lu et al. (ACS nano 2.5 (2008): 993-999).*
Tang et al. (Electrophoresis 2006, 27, 1303-1311).*
Simion et al. (Semiconductor Conference, 2008. CAS 2008. International. vol. 1. IEEE, 2008.).*
Ressine et al. (NanoBiotechnology 1.1 (2005): 93-103).*
Ma et al. ( Lab on a Chip 9.2 (2009): 232-238.).*
Ahn et al.( "Chemical SG-Selex on the Nanoporous Silicon Substrate Can Generate High Affinity ssDNA Aptamers Against Non-Soluble Chemicals"; 14th International Conference on Miniaturized Systems for Chemistry and Life Sciences; Oct. 3-7, 2010, Groningen, The Netherlands). (Year: 2010).*
Ahn, J., et al., "Sol-gel Material Optimization for Aptamer Biosensors", "Molecular and Cellular Toxicology", Jun. 30, 2008, pp. 100-105, vol. 4, No. 2.
Ahn, J., et al., "Sol-Gel Derived Nanoporous Compositions for Entrapping Small Molecules and Their Outlook toward Aptamer Screening", "Analytical Chemistry", Jan. 27, 2012, pp. 2647-2653, vol. 84.
Drott, J., et al., "Pore morphology inuence on catalytic turn-over for enzyme activated porous silicon matrices", "Thin Solid Films", 1998, pp. 161-166, vol. 330.
Drott, J., et al., "Porous Silicon Carrier Matrices in Micro Enzyme Reactors-Influence of Matrix Depth", "Mikrochim. Acta", 1999, pp. 115-120, vol. 131.
Finnskog, D., et al., "Integrated Protein Microchip Assay with Dual Fluorescent- and Maldi Read-Out", "Journal of Proteome Research", Sep. 11, 2004, pp. 988-994, vol. 3.
Kim, S., et al., "Improved Sensitivity and Physical Properties of Sol-Gel Protein Chips Using Large-Scale Material Screening and Selection", "Anal. Chem.", Sep. 27, 2006, pp. 7392-7396, vol. 78.
Park, S., et al., "Selection and elution of aptamers using nanoporous sol-gel arrays with integrated microheaters", "Lab on a Chip", Feb. 13, 2009, pp. 1206-1212, vol. 9.

(Continued)

*Primary Examiner* — Tracy Vivlemore
*Assistant Examiner* — Sahana S Kaup
(74) *Attorney, Agent, or Firm* — Hultquist, PLLC; Steven J. Hultquist (57) ABSTRACT

There is provided a sol-gel chip using a porous substrate for entrapping small molecules and a method for screening a small molecule-specific material using the same, and more particularly, a porous substrate sol-gel chip characterized in that a sol-gel composition for entrapping small molecules is spotted on a surface of the porous substrate, a method for manufacturing the porous substrate sol-gel chip for entrapping small molecules, and a method for screening a material specifically binding to the small molecules using the porous substrate sol-gel chip for entrapping small molecules. According to the present invention, the small molecules can be effectively entrapped in the chip and the inflow of aptamers can be maintained as compared with the existing methods and thus aptamers specific to an extensive range of small molecules can be more easily selected.

7 Claims, 4 Drawing Sheets

Specification includes a Sequence Listing.

(56) References Cited

OTHER PUBLICATIONS

Ressine, A., et al., "Macro-/Nanoporous Silicon as a Support for High-Performance Protein Microarrays", "Anal. Chem.", Nov. 8, 2003, pp. 6968-6974, vol. 75.
Ressine, A., et al., "Porous silicon protein microarray technology and ultra-/superhydrophobic states for improved bioanalytical readout", "Biotechnology Annual Review", 2007, pp. 149-200, vol. 13.
Ressine, A., et al., "Superhydrophobic Properties of Nanostructured-Microstructured Porous Silicon for Improved Surface-Based Bioanalysis", "Nanobiotechnology", Jul. 8, 2008, pp. 18-27, vol. 4.
Sevilimedu, A., et al., "TFIIB aptamers inhibit transcription by perturbing PIC formation at distinct stages", "Nucleic Acids Research", Apr. 10, 2008, pp. 3118-3127, vol. 36, No. 9.
Steinhauer, C., et al., "Biocompatibility of surfaces for antibody microarrays: design of macroporous silicon substrates", "Analytical Biochemistry", Nov. 19, 2004, pp. 204-213, vol. 341.
Note: For the non-patent literature citations that no month of publication is indicated, the year of publication is more than 1 year prior to the effective filing date of the present application.

\* cited by examiner

SOL-GEL CHIP USING POROUS SUBSTRATE FOR ENTRAPPING SMALL MOLECULES AND SCREENING METHOD OF SMALL MOLECULES SPECIFIC MATERIAL USING THEREOF

CROSS-REFERENCE TO RELATED APPLICATION

This application claims the priority under 35 U.S.C. § 119 of Korean Patent Application No. 10-2012-0014378 filed Feb. 13, 2012. The disclosure of Korean Patent Application No. 10-2012-0014378 is hereby incorporated herein by reference, in its entirety, for all purposes.

TECHNICAL FIELD

The present invention relates to a sol-gel chip using a porous substrate for entrapping small molecules and a method for screening a small molecule-specific material using the same, and more particularly, to a porous substrate sol-gel chip characterized in that a sol-gel composition for entrapping small molecules is spotted on a surface of the porous substrate, a method for manufacturing the porous substrate sol-gel chip for entrapping small molecules, and a method for screening a material specifically binding to small molecules using the porous substrate sol-gel chip for entrapping small molecules.

BACKGROUND ART

In recent years, advantages for sol-gel immobilization of biomaterials such as proteins and enzymes have been studied. Nano-structured complexes composed of sol-gel provide a liquid environment to the biomaterials to increase stability and retain biological activity. A sol-gel matrix restricts activity of biomolecules entrapped therein and thus prevents irreversible structural deformation, and this entrapment weakens molecular interactions between the sol-gel matrix and molecular residues exposed to the sol-gel matrix.

The present inventors developed a method for screening an appropriate sol-gel composition appropriate depending on molecular weights and/or diameters of several target molecules immobilized (Kim, S. et al., *Analytical chemistry*, 78: 7392, 2006), and confirmed sol-gel characterization including adhesive strength, spot shape, transparency, destruction, and entrapping, and successfully immobilized target materials including aptamers in the sol-gel network.

Sol-gel is widely used to entrap macromolecules, but there have been no reports yet that the small molecule compound was successfully entrapped and then allowed to bind to affinity ligand. A sol-gel composition is designed in order to entrap small molecules, but this composition is for attaching sol-gel to the existing substrate such as a microtiter plate polymer.

Meanwhile, porous silicon (PS) can be produced by anodic etching of monocrystalline silicon and offers a wide range of porous compositions based on the electrochemical process conditions. In the related arts where the porous silicon is used for protein immobilization, enzymes are covalently immobilized thereon (Ressine, A. et al., *Nanobiotechnol* 4:18, 2008; Ressine, A. et al., *Biotechnol Annu Rev* 13:149, 2007; Drott, J. et al., *Thin Solid Films* 330:161, 1998; Drott, J. et al., *MikroChimica Acta* 131:115, 1999), or antibodies are adsorbed onto a surface thereof (Ressine, A. et al., *Analytical chemistry*, 75:6968, 2003; Finnskog, D. et al., *J Proteome Res* 3: 988, 2004). However, the porous silicon compositions described in the related art documents is not appropriate for sol-gel based anchoring and aptamer selection.

Meanwhile, aptamers are probes recognizing specific molecules. Aptamers have high affinities to respective molecules and have extensive targets up to proteins, peptides, composite molecules of drugs, organic small molecules, and metal ions. It has been generally known that aptamers have higher affinity than antibodies.

Typically, aptamers are fabricated through repetition of in vitro selection or systematic evolution of ligand exponential enrichment (SELEX). In order to adapt SELEX to an appropriate tool for selecting high affinity aptamers targeting small molecule compounds, nitrocellulose membrane elution or affinity columns cannot be employed.

Accordingly, the present inventors endeavored to find substrates suitable to spot the sol-gel composition entrapping small molecules thereon, in order to solve the problem in that immobilization of small molecules is not easy in the sol-gel chip of the related art. As a result, the present inventors confirmed that, in the case where a sol-gel composition suitable to entrap small molecules is spotted on a porous silicon surface, an entrapped small molecule compound is well maintained in the spot and easily binds to a small molecule-specific aptamer, and completed the present invention.

DISCLOSURE

Technical Problem

An object of the present invention is to provide a method for immobilizing, onto a porous substrate, a sol-gel composition for entrapping small molecules, capable of allowing a smooth reaction with aptamers while well immobilizing small molecules in a sol-gel spot.

Another object of the present invention is to provide a method for screening a small molecule-specific aptamer by using a porous silicon sol-gel chip.

Technical Solution

According to an aspect of the present invention, there is provided a method for manufacturing a porous silicon sol-gel chip for entrapping small molecules, the method including: (a) preparing a porous substrate having pores with a depth of 100~3000 nm and a diameter of 100~1000 nm; and (b) spotting a sol-gel composition containing small molecules on a surface of the porous substrate.

According to another aspect of the present invention, there is provided a porous silicon sol-gel chip (PS-SG chip) for entrapping small molecules, in which a sol-gel spot entrapping small molecules is immobilized on a surface of a porous substrate having pores with a depth of 100~3000 nm and a diameter of 100~1000 nm.

According to still another aspect, there is provided a method for screening a small molecule-specific aptamer, the method including: (a) treating aptamer candidate groups on the porous silicon sol-gel chip for entrapping small molecules; and (b) selecting an aptamer specifically binding to the small molecule in a sol-gel spot.

According to still another aspect, there is provided a method for screening a material specifically binding to a small molecule by using a porous silicon sol-gel chip in which a sol-gel spot entrapping a small molecule compound is immobilized on a surface of a porous substrate, the method including: (a) treating material candidate groups capable of binding to the small molecule compound on a porous silicon sol-gel chip for entrapping small molecules; (b) selecting and isolating a material specifically binding to the small molecule compound in a sol-gel spot; and (c) identifying the isolated material specifically binding to the small molecule compound.

Advantageous Effects

As set forth above, the present invention can effectively entrap the small molecule compound in a sol-gel structure and maintain the inflow of aptamers, as compared with the existing methods, and thus can more easily screen aptamers specific to an extensive range of small molecules.

BRIEF DESCRIPTION OF DRAWINGS

FIGS. 6A and 6B are for illustrating an interaction between BPA, which is a target small molecule material, and a specific aptamer thereof on a PS-SG chip, and FIG. 6A schematically shows the interaction between BPA and the aptamer and a method for detecting the specific aptamer and FIG. 6B shows pictures of fluorescent signals exhibited by allowing the BPA aptamer to specifically bind to the sol-gel spot containing BPA.

FIGS. 7A and 7B are for confirming that PS-SG chips are heat-treated to elute aptamers, and FIG. 7A shows elution of the aptamers from the sol-gel spots by heat treatment and FIG. 7B shows a PCR amplification result of a collected aptamer.

DETAILED DESCRIPTION OF THE EMBODIMENTS

In one aspect, the present invention is directed to a method for manufacturing a porous silicon sol-gel chip for entrapping small molecules, the method comprising: (a) preparing a porous substrate having pores with a depth of 100~3000 nm and a diameter of 100~1000 nm; and (b) spotting a sol-gel composition containing small molecules on a surface of the porous substrate.

Figure 1:
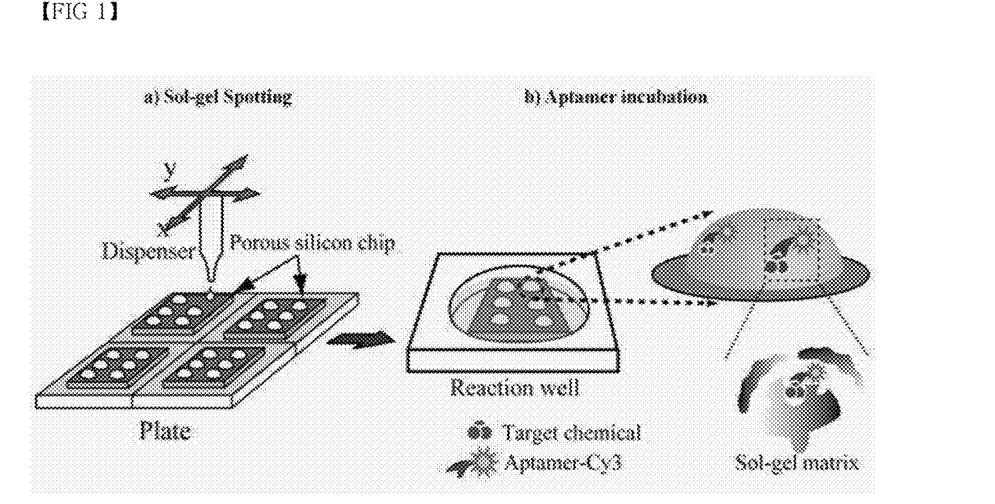
FIG. 1 is a conceptual view of a porous silicon sol-gel chip platform according to the present invention.

The porous silicon sol-gel chip (PS-SG chip) according to the present invention may be used as a flatform finding an aptamer specifically binding to a small molecule compound (FIG. 1). A porous silicon surface used herein is newly invented substrate to physically immobilize a sol-gel spot thereon.

In the present invention, the porous substrate may be selected from a group consisting of silicon, glass, and plastic. A porous surface of the porous substrate may be fabricated by anodic etching, chemical etching, patterning, carbon nanotube forming, or polyvinyl acetate (PVAc) coating, but is not limited thereto. Any method that can form pores having a depth of 100~3000 nm and a diameter of 100~1000 nm in the surface of the substrate may be employed without limitation.

In one embodiment of the present invention, the porous silicon substrate may be fabricated by subjecting monocrystalline silicon to anodic etching at a current of 0.5~10 mA/Cm$^2$ for 5~20 minutes.

If the amount of current for anodic etching is less than 0.5 mA/Cm$^2$, depths and sizes of pores formed in the silicon surface are too small, resulting in degrading the immobilizing ability of the sol-gel spot. If more than 10 mA/Cm$^2$, depths and sizes of the pores are large, and thus, at the time of assaying using the chip, compounds such as aptamers and the like are trapped between the pores, resulting in decreasing efficiency in selecting an aptamer specific to a small molecule compound.

In addition, if the time for anodic etching is 5 minutes or less, depths and sizes of pores formed are too small, resulting in degrading the immobilizing ability of the sol-gel spot. If 20 minutes or more, depths and sizes of the pores are large, and thus, at the time of assaying using the chip, compounds such as aptamers and the like are trapped between the pores, resulting in decreasing efficiency in selecting an aptamer specific to a small molecule compound.

In another aspect of the present invention, glass as the support is subjected to chemical etching using a hydrofluoric acid (HF) solution, to fabricate the porous surface. In the case of glass etching using hydrofluoric acid (HF), the same hydrofluoric acid solution that is used in fabricating the porous silicon substrate is used. The change in porosity property of the surface according to the exposure time of glass to the hydrofluoric acid solution (1 minute, 3 minutes, 5 minutes, 10 minutes, 20 minutes, 30 minutes, and 1 hour) is measured, and as a result, at the time of etching for 10~20 minutes, pores having a depth of 100~3000 nm and a diameter of 100~1000 nm may be fabricated in the surface of the glass substrate.

In still another aspect of the present invention, in order to fabricate a carbon nanotube (CNT) coating porous glass surface, a glass piece is immersed in a CNT solution so that CNTs are adsorbed onto the glass. In order to fabricate CNT coating glass, a glass sample is treated with a mixture solution of sulfuric acid/peroxide (3:1, V:V) for 10 minutes, and then the glass piece is immersed in a CNT solution of 0.1 mg/m using ortho-dichlorobenzene as a solvent for 10 seconds. As a result, it may be confirmed that nanotubes having a depth of 100~3000 nm are formed on the surface of the glass substrate.

In still another aspect of the present invention, in order to form a surface of plastic (polymethyl methacrylate, PMMA) by using polyvinyl acetate (PVAc), a mixture of benzene as a solvent and 1~10% of PVAc is coated on the plastic PMMA substrate by a spin coating method. The porous surface having pores with a depth of 100~3000 nm and a diameter of 100~1000 nm may be fabricated under conditions of RPM: 2000~6000, REM: 0~10 seconds, and spin time: 3~20 seconds.

In one embodiment of the present invention, the pores are formed in the silicon surface by using an anodic etching method. Any conventional method that can form pores each having an average depth of 663.45 nm and an average diameter of 445.52 nm, such as a patterning method or the like, may be employed.

In the present invention, if the depth of the pore formed in the silicon wafer is 100 nm or smaller, the immobilizing ability of the sol-gel spot may be degraded. If 3000 nm or greater, compounds such as aptamers and the like may be trapped between the pores, resulting in increasing a background signal, at the time of assaying using the chip.

Similarly, in the present invention, if the diameter of the pore formed in the silicon wafer is 100 nm or smaller, the immobilizing ability of the sol-gel spot may be deteriorated. If 1000 nm or greater, compounds such as aptamers and the like may be trapped between the pores, resulting in decreasing the selecting ability of an aptamer specific to a small molecule compound, at the time of assaying the chip.

Figure 2:
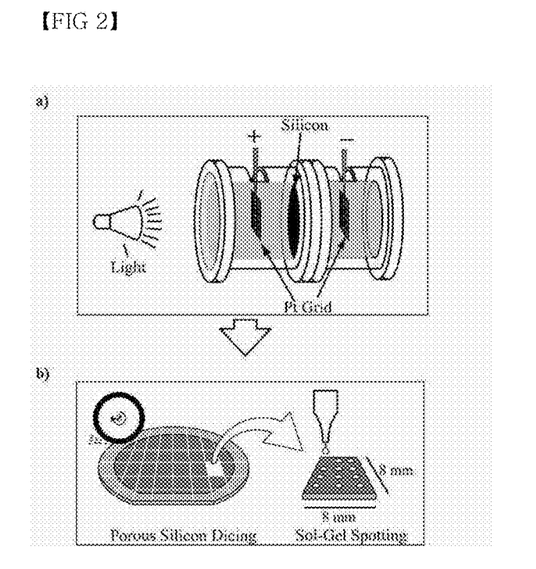
FIG. 2A shows a method for preparing a porous silicon surface.
FIG. 2B shows a method for spotting a sol-gel composition containing small molecules on a super-porousified silicon wafer after dicing.

In the present invention, the porous silicon (Si) surface may be fabricated by anodic dissolution of monocrystalline silicon dissolved in hydrofluoric acid (HF) (FIG. 2A). In order to manufacture the porous silicon sol-gel chip, in the comparative example of the present invention, a super-porousified silicon wafer having high porosity is diced into a square shape, and then a mixture of sol-gel (for example, Composition A of Example 2) and a small molecule is spotted on a surface of the chip (FIG. 2B).

In the present invention, the super-porousified silicon wafer used as a comparative example has a pore depth of 3000~4000 nm and a pore diameter of 1000~2000 nm.

A surface of the super-porousified chip having micro- and nano-morphology has good property in increasing the probe concentration in the application of a microarray, but is not in an optimized state for immobilizing the sol-gel chip entrapping small molecule compounds.

Figure 3:
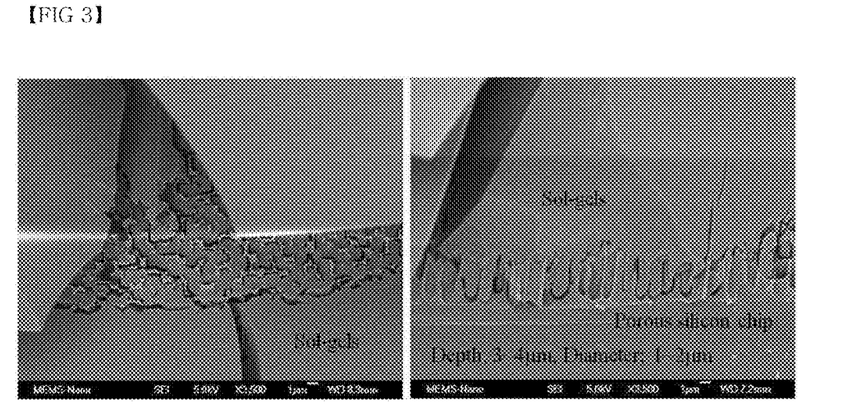
FIG. 3 shows SEM images confirming voids appearing on a boundary of a sol-gel droplet spotted on a super-porousified silicon surface of the related art.

Voids between the condensed sol-gel and the surfaces of micropores of porous silicon were uniformly observed on the super-porousified surface (FIG. 3). During the assay, the aptamers may be non-specifically trapped in the space, and thus non-specific aptamers may be selected at a high ratio.

Figure 4:
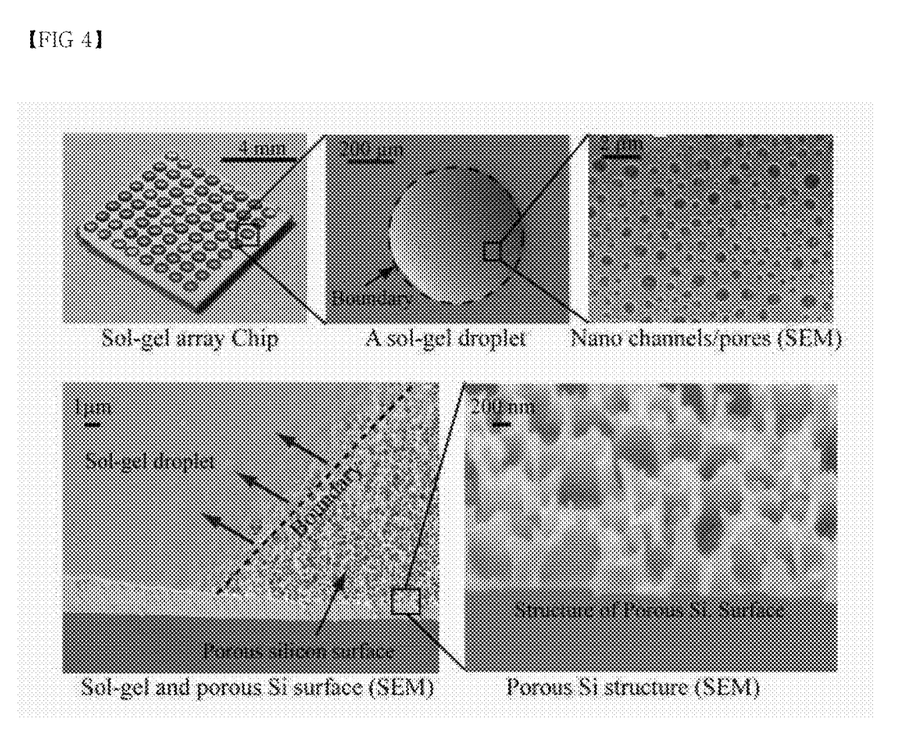
FIG. 4 shows SEM images of a sol-gel spot on a PS-SG chip according to the present invention.

As shown in FIG. 4 of the present invention, assay conditions were improved so that a thinner porous layer having smaller pores is formed by the change in porousification conditions of the silicon surface, to thereby firmly immobilize the sol-gel and decrease the ratio of selecting non-specific aptamers. When the porous silicon surface employed in the porous silicon sol-gel chip of the present invention was confirmed by an SEM image, it was confirmed that the porous silicon surface has a thinner porous structure (FIG. 4) as compared with the existing micro/nano-sized super-porousified surface structure (FIG. 3).

Therefore, the porous substrate of the present invention is characterized by having micro or nano-sized pores.

An upper left image of FIG. 4 shows a PS-SG chip of the present invention; an upper middle image of FIG. 4 shows an SEM image of a single sol-gel spot; and an upper right image of FIG. 4 shows an enlarged view of the single sol-gel spot, which may confirm nano-sized pores and channels. A lower left image of FIG. 4 shows a boundary of the sol-gel spot, which may confirm that the sol-gel is immobilized on the porous silicon surface, and a lower right image of FIG. 4 is an enlarged view of a micro-/nano-porous silicon surface network. According to the foregoing structure, the binding between the sol-gel including small molecules and the porous silicon surface was very much improved, and the void trapping non-specific aptamers was decreased.

In the present invention, the small molecules may be selected from a group consisting of metabolites, toxins, and insecticidal compounds, and the sol-gel composition may include one or a combination of two or more selected from a group consisting of methyltriethoxysilane (MTES), ethyltriethoxysilane (ETrEOS), sodium silicate, tetramethyl orthosilicate (TMOS), tetraethyl orthosilicate (TEOS), tetramethoxysilicate (TMS) methyltriethoxysilane (MTES), ethyltriethoxysilane (ETrEOS), sodium silicate, tetramethyl orthosilicate (TMOS), tetraethyl orthosilicate (TEOS) and tetramethoxysilicate (TMS), methyltrimethoxysilicate (MTMS), 3-aminotrimethoxysilane (3-ATMS), polyglycerylsilicate (PGS), diglycerylsilane (DGS), polyvinylacetate, polyvinylpyrrolidone, glyceryl metaacrylate, hydroxyethyl acrylate, N,N-dicusinimidilcarbonate (DSC), 1,3,5-trimethylbenzene, cetyltrimethylammonium chloride, cetyltrimethylammonium bromide, 3-(triethoxysily) propyl sucinic unhydride, N-(3-triethoxysily propyl)-4-hydroxy butylamide (SIT8189.5), N-(triethoxysilyl propyl) gluconamide (SIT8189.0), pluronic L121, tetramethyl ammonium hydroxide, SolB III (aminopropyltriethoxysilane (APTES)), 3-glycidoxypropyltrimethoxysilane (GPTMOS), N-triethoxysilylpropyl-O-polyethylene oxide urethane (PEOU), glycerol, PEG200, PEG400, PEG600, PEG1350, and PEG8000.

The small molecule used in the example of the present invention was bisphenol A (BPA), and was first entrapped in the porous silicon sol-gel chip. The sol-gel composition was immobilized to the porous substrate in a microarray type.

In the present invention, the porous silicon sol-gel chip entrapping the small molecules may be characterized by being used for selecting aptamers specific to the small molecules.

In another aspect, the present invention is directed to a porous silicon sol-gel chip for entrapping small molecules, characterized in which a sol-gel spot entrapping the small molecule compound is immobilized on a surface of a porous substrate having pores having a depth of 100~3000 nm and a diameter of 100~1000 nm.

The technology of entrapping proteins and antibodies in the specific sol-gel composition was established in recent protein chip studies. The present invention confirmed a method of entrapping small molecules in sol-gel. In one embodiment of the present invention, fluorescent indicators (fluorescein sodium salt, 376.27 Da)) with two kinds of sol-gel formulations, Formula A (SolB 127.5%; SolB II 10%; SolB H 12.5%; SolB S 12.5%; DW 25%) and Formula B (SolB 125%; SolB II 7.5%; SolB III 5%; SolB H 12.5%; SolB S 12.5%; DW 25%) of SolB Complete Kit (PCL Company, Korea, Homepage: pcichip.com) were spotted, and after washing with phosphate buffered saline (PBS), it was confirmed whether or not the fluorescence of fluorescein was maintained. As a result, it was confirmed that the entrapping of small molecules was successfully maintained in the sol-gel Formula A (Table 1).

Here, SolB I is at least one first silicate monomer selected from a group consisting of methyltriethoxysilane (MTES), ethyltriethoxysilane (ETrEOS), sodium silicate, tetramethyl orthosilicate (TMOS), tetraethyl orthosilicate (TEOS) and tetramethoxysilicate (TMS) methyltriethoxysilane (MTES), ethyltriethoxysilane (ETrEOS), sodium silicate, tetramethyl orthosilicate (TMOS), tetraethyl orthosilicate (TEOS), and tetramethoxysilicate (TMS).

SolB II is at least one second silicate monomer selected from a group consisting of methyltrimethoxysilicate (MTMS), 3-aminotrimethoxysilane (3-ATMS), polyglycerylsilicate (PGS), diglycerylsilane (DGS), polyvinylacetate, polyvinylpyrrolidone, glyceryl metaacrylate, hydroxyethyl acrylate, N,N-dicusinimidilcarbonate (DSC), 1,3,5-trimethylbenzene, cetyltrimethylammonium chloride, cetyltrimethylammonium bromide, 3-(triethoxysily) propyl sucinic unhydride, N-(3-triethoxysily propyl)-4-hydroxy butylamide (SIT8189.5), N-(triethoxysily)propyl)gluconamide (SIT8189.0) 50%, pluronic L121, and tetramethyl ammonium hydroxide. SolB III is at least one additive selected from a group consisting of aminopropyltriethoxysilane (APTES), 3-glycidoxypropyltrimethoxysilane (GPTMOS), N-triethoxysilylpropyl-O-polyethylene oxide urethane (PEOU), glycerol, PEG200, PEG400, PEG600, PEG1350, and PEG8000.

SolB H is composed of a solution selected from a group consisting of HCl, $H_2SO_4$, $HNO_3$ and $CH_3COOH$, SolB S (buffer), and distilled water (DW). As the SolB kit used in the present invention, the SolB complete kit purchased from the PCL Company (Korea) was used.

Meanwhile, the sol-gel spot containing small molecules, which was spotted on a surface of the poly(methyl methacrylate) (PMMA) micro well, exhibited low adhesive ability with the plastic surface. At the first stage of the assay, when washing with the PBS buffer, all spots were washed out. Even the use of Sol-Gel Composition A optimized in Example 2 of the present invention came to the same results.

TABLE 1

Yield of spots after washing and scratching on the porous Si and PMMA surface

|  | Spotting | Washing | Scratching |
|---|---|---|---|
| Porous Si | 64 (8 × 8) | 64 (100%) | 63 (98.4%) |
| PMMA | 64 (8 × 8) | 0 (0%) | 0 (0%) |

Table 1 shows the number of spots maintained after washing and scratching sol-gel spots (64 spots) spotted on the porous silicon (Si) surface and sol-gel spots (64 spots) spotted on the poly(methyl methacrylate) (PMMA) surface.

It may be seen that, for the PMMA surface, all the spots were washed out during a washing procedure, and 64 spots on the porous silicon surface used in the present invention were maintained even during the washing procedure and the scratching procedure.

In the example of the present invention, a chip immobilizing a sol-gel spot entrapping bisphenol A (BPA) as a small molecule on the porous silicon surface (PS-SG chip) was manufactured, and the BPA aptamer fluorescent-labeled on the chip was treated and washed. As a result, it was confirmed that the aptamer successfully permeated into the sol-gel chip and bound to the BPA, and thus exhibited fluorescence.

In still another aspect, the present invention is directed to a method for screening a small molecule-specific aptamer, the method comprising: (a) treating aptamer candidate groups on the porous silicon sol-gel chip for entrapping small molecules; and (b) selecting an aptamer specifically binding to a small molecule compound in a sol-gel spot. The aptamer screening method is characterized by using a porous silicon sol-gel chip in which the sol-gel spot entrapping a small molecule compound is immobilized on a surface of the porous substrate.

The PS-SG chip of the present invention may be used in selecting an aptamer to a small molecule target material in vitro by using a systematic evolution of ligands by exponential enrichment (SELEX) protocol. The SELEX is a screening technology of intensively screening very specific ligands or aptamers by repeating selection and amplification in a nucleic acid library having huge combinations ($10^{13}$~$10^{15}$). In the existing SELEX procedure, a small molecule target needed to chemically bind to a substrate by a linker molecule or a mass carrier at a first stage. In this case, suitability in physical/chemical properties of a substrate with respect to a target material needed to be considered, and the binding efficiency of the target material and the substrate needed to be considered in a screening procedure for each stage of the SELEX. Some aptamers were successfully isolated by the existing method, but many compounds were not efficiently immobilized during the SELEX procedure.

In the present invention, the PS-SG chip of the present invention entrapping small molecules and maintaining the inflow of aptamers can open the road to develop aptamers specific to a wide range of small molecules.

In the present invention, the method for screening a small molecule-specific aptamer may further include: c) heat-treating the porous substrate sol-gel chip to which an aptamer binds, to collect an eluted aptamer.

In the SELEX technology in the related art, methods of collecting aptamers from the aptamer-target complexes have been reported (Sevilimedu, A. et al., *Nucleic Acids Res* 36:3118, 2008, Ahn, J. Y. et al., *Mol. Cell. Toxicol.*, 4:100, 2008, Park, S. et al., *Lab Chip*, 9:1206, 2009). The aptamers binding to the target material are completely collected, so that the number of cycles necessary for the SELEX procedure can be decreased and the resources can be saved. The means for releasing the bound aptamer may be determined depending on the property of the target material binding to the aptamer. In the present invention, a method of "heat-eluting" the aptamer from the target material was established. Since the structure of the aptamer is determined by hydrogen bonds between bases constituting the aptamer, the structure is deformed by heat to lose the binding force with the target.

In the present invention, the aptamer binding to the target material of the sol-gel chip is eluted by heat treatment, followed by collection and PCR amplification, to thereby confirm the collection of aptamers. This confirmed that the aptamer may be efficiently collected without excessive denaturation of an aptamer sequence in the PS-SG chip.

In another aspect, the present invention is directed to a method for screening a material specifically binding to a small molecule by using a porous silicon sol-gel chip in which a sol-gel spot entrapping a small molecule compound is immobilized on a surface of a porous substrate, the method comprising: (a) treating material candidate groups capable of binding to the small molecule compound on a porous silicon sol-gel chip for entrapping small molecules; (b) selecting and isolating a material specifically binding to the small molecule compound in a sol-gel spot; and (c) identifying the isolated material specifically binding to the small molecule compound.

In the present invention, as the material specifically binding to the small molecule compound, any material that can be combined with the small molecule compound immobilized in the sol-gel spot, such as protein, aptamer, antibody, enzyme, and the like, may be screened. The bound material may be identified by a general method, and for example, methods such as MASS, MALDI-TOFF, NMR, and the like may be employed.

Hereinafter, the present invention will be described in detail with reference to the examples. These examples are only for exemplifying the present invention, and it will be obvious to those skilled in the art that the scope of the present invention is not construed to be limited to these examples.

Example 1: Fabrication of Porous Silicon Surface

Porous silicon (PS) has an anisotropic and nanocrystal silicon structure having a high surface area, and may be fabricated from monocrystalline silicon by a galvanostatic electrochemical or photochemical etching in the presence of hydrofluoric acid (HF). The above procedure is controlled by several factors, such as density, etching time, crystal direction, silicon dopant type, doping level, illumination, electrode constitution, temperature, surface roughness, and the like.

The fabrication of the porous silicon was described in several documents (Steinhauer, C et al., *Anal Biochem*, 341: 204, 2005; Finnskog, D. et al., *J Proteome Res*, 3: 988, 2004). Shortly, a two-compartment electrochemical cell having sapphire glass (Melees Griot BV) formed on one-sided surface was used for illumination at the time of anodizing, and the wafer was etched at a constant current of 2 mA/Cm$^2$ for 10 minutes.

The pores formed in the surface of the silicon substrate fabricated in the present example were confirmed by SEM, and as a result, had an average depth of 663.45 nm and an average diameter of 445.52 nm.

Example 2: Establishment of Sol-Gel Composition for Immobilizing Small Molecule Compound Sol-gel was spotted on a surface of a porous silicon chip, and the sol-gel material for immobilizing the small molecule compound was prepared by the method recommended from the manufacture company (SolB complete kit, PCL Company, Korea, website: pcichip.com). The fluorescent indicator was prepared with two different sol-gel formulations to investigate the immobilization performance. That is, the two sol-gel formulations (Formula-A: SolB I 27.5%; SolB II 10%; SolB H 12.5%; SolB S 12.5%; DW 25%, Formula-B: SolB 125%; SolB II 7.5%; SolB III 5%; SolB H 12.5%; SolB S 12.5%; DW 25%) and the fluorescent indicator were uniformly mixed with the SolB agent to prepare sol-gel microarrays.

SolB I is at least one first silicate monomer selected from a group consisting of methyltriethoxysilane (MTES), ethyl-triethoxysilane (ETrEOS), sodium silicate, tetramethyl orthosilicate (TMOS), tetraethyl orthosilicate (TEOS) and tetramethoxysilicate (TMS) methyltriethoxysilane (MTES), ethyltriethoxysilane (ETrEOS), sodium silicate, tetramethyl orthosilicate (TMOS), tetraethyl orthosilicate (TEOS), and tetramethoxysilicate (TMS).

SolB II is at least one second silicate monomer selected from a group consisting of methyltrimethoxysilicate (MTMS), 3-aminotrimethoxysilane (3-ATMS), polyglycerylsilicate (PGS), diglycerylsilane (DGS), polyvinylacetate, polyvinylpyrrolidone, glyceryl metaacrylate, hydroxyethyl acrylate, N,N-dicusinimidilcarbonate (DSC), 1,3,5-trimethylbenzene, cetyltrimethylammonium chloride, cetyltrimethylammonium bromide, 3-(triethoxysily) propyl sucinic unhydride, N-(3-triethoxysily propyl)-4-hydroxy butylamide (SIT8189.5), N-(triethoxysily)propyl)gluconamide (SIT8189.0) 50%, pluronic L121, and tetramethyl ammonium hydroxide. SolB III is at least one additive selected from a group consisting of aminopropyltriethoxysilane (APTES), 3-glycidoxypropyltrimethoxysilane (GPTMOS), N-triethoxysilylpropyl-O-polyethylene oxide urethane (PEOU), glycerol, PEG200, PEG400, PEG600, PEG1350, and PEG8000.

SolB H is composed of a solution selected from a group consisting of HCl, $H_2SO_4$, $HNO_3$ and $CH_3COOH$, SolB S (buffer), and distilled water (DW).

The fluorescent indicator was diluted into 1525 nM, 781 nM, 391 nM, and 195 nM for each single spot, and then spotted in a 96-well type micro-plate, followed by gelation for 16 hours. After that, 100 μl of a PBS solution was added thereto, and then while the reaction is allowed to proceed for 0 hour, 1 hour, 3 hours, and 5 hours, the light intensity of fluorescent indicator was measured and the results thereof were tabulated in FIG. 5.

Figure 5:
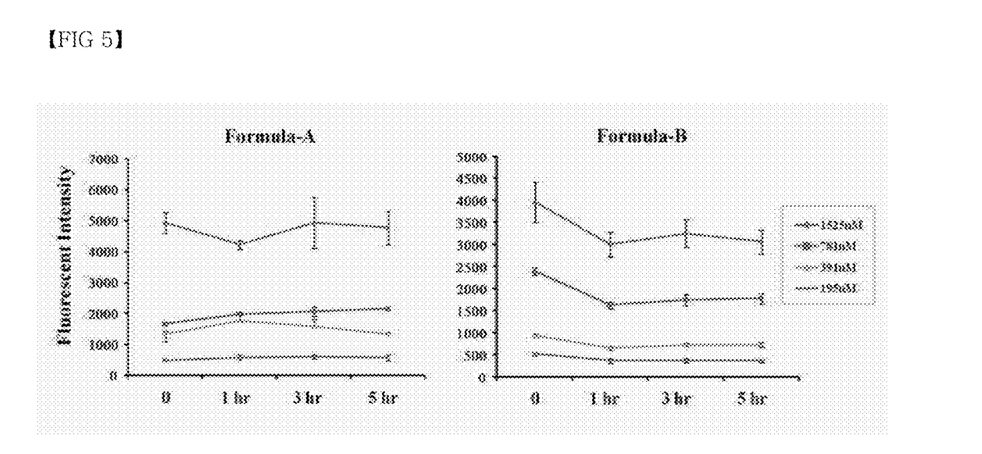
FIG. 5 shows fluorescent change of spots prepared by Sol-Gel Formula A and B each entrapping a fluorescent indicator (Fluorescein).

The fluorescent intensity was maintained for the overall time for Sol-Gel Formula A, and the fluorescent intensity was rapidly reduced for elapse of one hour for Sol-Gel Formula B. This shows that Formula A well entraps the fluorescent indicator and thus release of the fluorescent indicator does not occur, but Formula B allows the release of fluorescence due to weak entrapment force thereof.

Therefore, Sol-Gel Formula A had superior ability to entrap the small molecule compound in an inner pore, and thus Sol-Gel Formula A was used to sol-gel-entrap small molecules for aptamer binding.

Example 3: BPA and BPA Aptamer Microarray

As a target analyte of a sol-gel microarray for detecting small molecules, BPA (bisphenol A; 4,4'-dihydroxy-2,2-diphenylpropane, Sigma-Aldrich, USA) was used. BPA was dissolved in 50% dimethyl formamide (DMF) to have a final concentration of 100 mM.

The sol-gel mixture containing the target material, together with a negative control not entrapping a target material and a positive control entrapping Cy3 fluorescent indicator, was spotted by using a non-contact type dispenser, sciFLEXARRAYER S11 (Scieninon AG, Germany), and the volume of a single spot was measured by using an automatic volume confirmation (sciDROPVOLUME) software.

The sol-gel material entrapping BPA (100 mM) was spotted on the surface of the porous silicon by using the non-contact type dispenser, and the volume of a single droplet was about 4 nL. The distance between spots was set 400 μm, and each chip included 64 spots in an array of 8×8. The sol-gel entrapping BPA was spotted in an alphabet shape of 'L', 'U', 'N', and 'D', and the negative control sol-gel composition not containing BPA was spotted in the rest of the spaces other than the alphabet.

In order to confirm the binding of BPA and the specific aptamer thereof, the BPA aptamer was labeled with Cy3-UTP (GeneChem Inc., Korea) by using terminal deoxynucleotidyl transferase.

The anti-BPA aptamer sequence is as follows.

```
Anti-BPA aptamer sequence
                                        (SEQ. ID. No. 1)
5'- GGG CCG TTC GAA CAC GAG CAT GCC GGT GGG TGG

TCA GGT GGG ATA GCG TTC CGC GTA TGG CCC AGC GCA

TCA CGG GTT CGC ACC AGG ACA GTA CTC AGG TCA TCC

TAG -3'
```

A reaction mixture solution where 5× reaction buffer 4 μl, ssDNA aptamer 0.5 nmol, Cy3-dUTP 1 nmole, and 30U TdT enzyme were contained in a 20 μl reaction solution was prepared, and then the reaction was allowed to proceed at 37° C. for 4 hours. The fluorescent-labeled DNA aptamer was precipitated with ethanol at −70° C. In order to allow the aptamer to form a structure, 100 pmole BPA aptamer was dissolved in 50 μl of 1×PBS, and heated at 95° C. for 10 minutes, and then cooled at room temperature for 3 hours. The PS-SG chip entrapping BPA was treated with a blocking buffer (containing 20 μg/mL tRNA, in 1×PBS) for 2 hours, and was reacted by using 2 μM of Cy3-labeled BPA aptamer for 1 hour. The chip after the reaction was washed with a washing solution (0.2% Tween-20 in 1×PBS) for 15 minutes three times, and then dried for 10 minutes. The sol-gal array results were scanned and analyzed by using a fluorescent scanner (Typhoon FLA9000, GE Healthcare).

Figure 6:
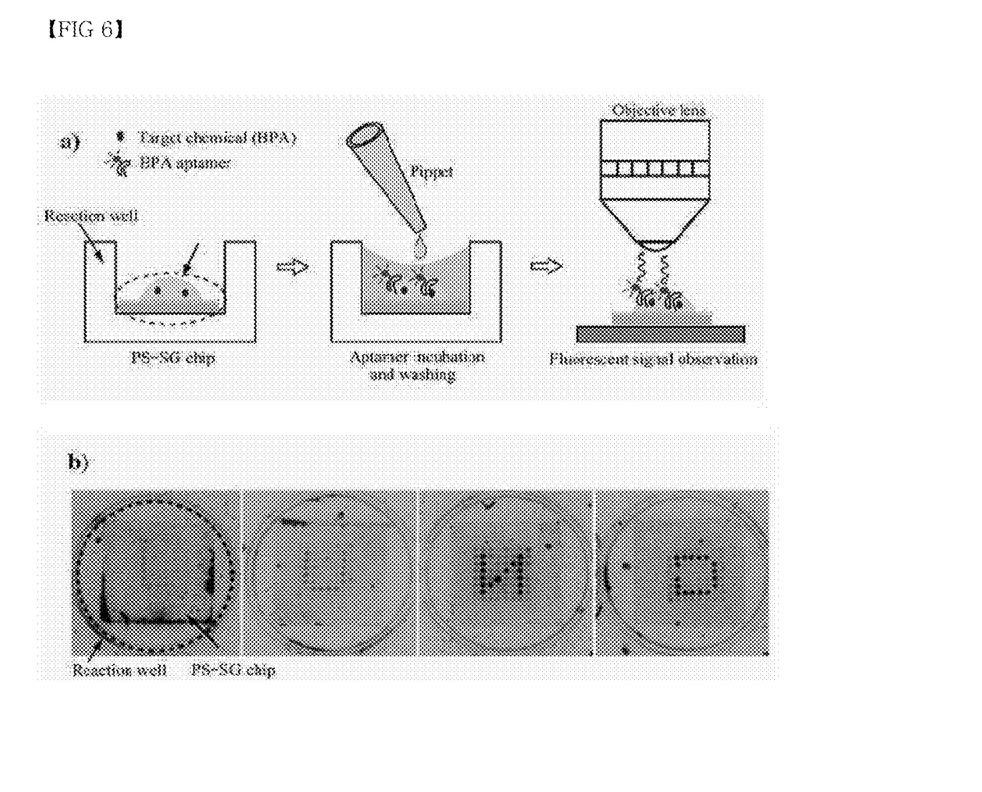

FIG. 6A shows a method of detecting a spot by using a scanner, in which BPA entrapped in the PS-SG chip and the fluorescent-labeled BPA aptamer are combined to exhibit a fluorescent signal on the chip.

As a result, as shown in FIG. 6B, it may be confirmed that the sol-gel spots entrapping BPA was detected in an alphabet shape of 'L', 'U', 'N', and 'D' by the fluorescent-labeled BPA aptamer.

For this reason, it may be seen that the sol-gel entrapping the small molecule compound such as BPA is successfully immobilized onto the porous silicon surface, and the entrapped small molecule compound can specifically bind to the aptamer.

Example 4: Collection of Aptamer by Heat Treatment

The sol-gel composition entrapping BPA was spotted in an alphabet shape of "H", and was subjected to binding reaction with the specific aptamer, and then washed with 300 μl of PBS. One chip was heat-treated at 95° C. for 1 minute, and the other chip was heat-treated for 5 minutes. After the heat treatment, the released aptamer was collected by ethanol precipitation, and PCR-amplified by 15 cycles.

PCR conditions were as follows: initial heat treatment at 94° C. for 5 minutes, 15 cycles of 94° C., 55° C., and 72° C. for 30 seconds for each temperature, and then final elongation for 7 minutes. PCR products (86 bp) were confirmed by electrophoresis using 2% agaros gel.

Figure 7:
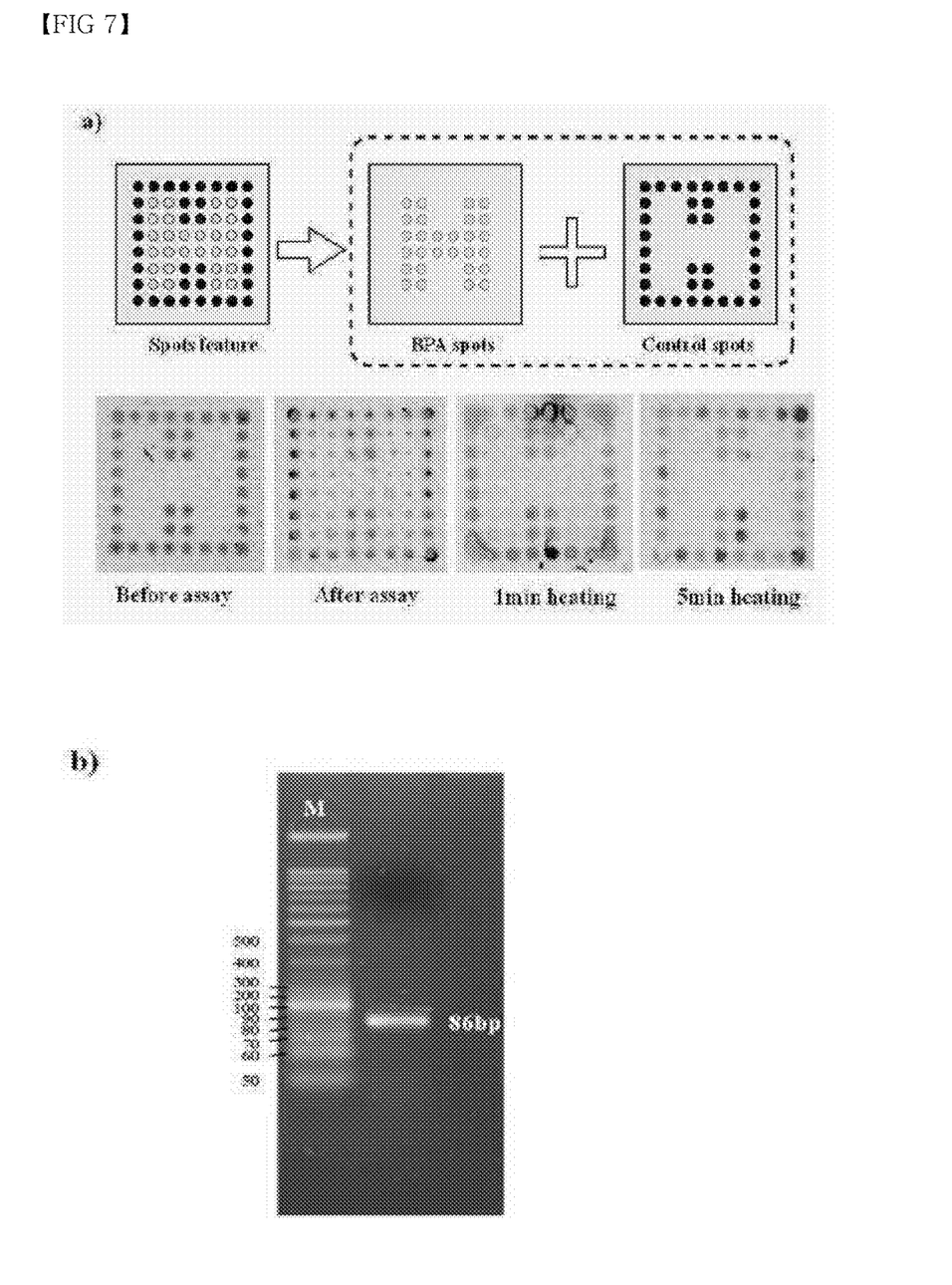

In the present invention, after the heat treatment, the fluorescent signal of the aptamer combined with the sol-gel spot was monitored. As shown in FIG. 7A, the aptamer-combined signal was completely vanished after heat treatment at 95° C. for 5 minutes, and 86 bp of aptamer collected from the PS-SG chip was amplified, and then confirmed through electrophoresis (FIG. 7B).

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

wherein said small molecules are selected from the group consisting of metabolites, toxins, and insecticidal compounds, the method comprising:
  (a) forming, in a porous substrate having pores with a depth of 3000 nm or more and a diameter of 1000 nm or more, a surface layer having pores with a depth of 100 to less than 3000 nm and a diameter of 445 nm to less than 1000 nm; and
  (b) spotting a sol-gel composition on said surface layer of the porous substrate, to immobilize the sol-gel composition thereon, wherein the sol-gel composition contains small molecules for which said aptamers are to be selected, so that specific aptamers targeting the small molecules will bind to the small molecules in the sol-gel spotted on the surface layer and non-specific aptamers will be prevented at a boundary of the spotted sol-gel composition from being trapped by voids and pores of the porous substrate,
wherein the sol-gel composition comprises 27.5% of SolB I; 10% of SolB II; 12.5% of SolB H; 12.5% of SolB S(buffer) and 25% of DW,
wherein SolB I is at least one first silicate monomer selected from a group consisting of methyltriethoxysilane (MTES), ethyltriethoxysilane (ETrEOS), sodium silicate, tetramethyl orthosilicate (TMOS), tetraethyl orthosilicate (TEOS) and tetramethoxysilicate (TMS) methyltriethoxysilane (MTES), ethyltriethoxysilane (ETrEOS), sodium silicate, tetramethyl orthosilicate (TMOS), tetraethyl orthosilicate (TEOS), and tetramethoxysilicate (TMS),
SolB II is at least one second silicate monomer selected from a group consisting of methyltrimethoxysilicate (MTMS), 3-aminotrimethoxysilane (3-ATMS), polyglycerylsilicate (PGS), diglycerylsilane (DGS), polyvinylacetate, polyvinylpyrrolidone, glyceryl metaacrylate, hydroxyethyl acrylate, N,N-dicusinimidilcarbonate (DSC), 1,3,5-trimethylbenzene, cetyltrimethylammonium chloride, cetyltrimethylammonium bromide, 3-(triethoxysily) propyl sucinic unhydride, N-(3-triethoxysily propyl)-4-hydroxy butylamide (SIT8189.5), N-(triethoxysilyl propyl) gluconamide (SIT8189.0) 50%, pluronic L121 (polyoxypropylene-polyoxyethylene block copolymer), and tetramethyl ammonium hydroxide, and
SolB H is a solution selected from a group consisting of HCl, $H_2SO_4$, $HNO_3$ and $CH_3COOH$.

What is claimed is:
1. A method for manufacturing a porous substrate-sol-gel chip for selecting aptamers targeting small molecules,

2. The method of claim 1, wherein the porous substrate is selected from a group consisting of silicon, glass, and plastic.

3. The method of claim 1, wherein the porous surface of the porous substrate is fabricated by anodic etching, chemical etching, patterning, carbon nanotube forming, or polyvinyl acetate (PVAc) coating.

4. The method of claim 2, wherein the porous substrate is fabricated by subjecting monocrystalline silicon to anodic etching at a current of 0.5~10 mA/$Cm^2$ for 5~20 minutes.

5. The method of claim 1, wherein the small molecules are metabolites.

6. The method of claim 1, wherein the small molecules are toxins.

7. The method of claim 1, wherein the small molecules are insecticidal compounds.

* * * * *

SEQUENCE LISTING

<160> NUMBER OF SEQ ID NOS: 1

<210> SEQ ID NO 1
<211> LENGTH: 108
<212> TYPE: DNA
<213> ORGANISM: Artificial
<220> FEATURE:
<223> OTHER INFORMATION: Aptamer of BPA

<400> SEQUENCE: 1
gggccgttcg aacacgagca tgccggtggg tggtcaggtg ggatagcgtt ccgcgtatgg    60
cccagcgcat cacgggttcg caccaggaca gtactcaggt catcctag                 108